United States Patent [19]

Deluhery

[11] Patent Number: 5,040,546
[45] Date of Patent: Aug. 20, 1991

[54] PATIENT POSITIONING DEVICE AND METHOD

[75] Inventor: James G. Deluhery, Madison, Wis.

[73] Assignee: Lunar Corporation, Madison, Wis.

[21] Appl. No.: 454,145

[22] Filed: Dec. 21, 1989

[51] Int. Cl.⁵ .............................................. A61G 13/00
[52] U.S. Cl. ..................................... 128/845; 128/870; 269/328; 378/204; 5/431
[58] Field of Search ................... 128/68, 70, 845, 870, 128/876; 378/204, 208, 209, 210; 269/322, 328; 5/431, 513

[56] References Cited

U.S. PATENT DOCUMENTS

| | | | |
|---|---|---|---|
| 2,656,469 | 10/1953 | Laur | 378/208 X |
| 3,087,059 | 4/1963 | Eveland | 378/209 X |
| 3,245,382 | 4/1966 | Easley et al. | 128/870 X |
| 3,581,088 | 5/1971 | Engels | 269/322 X |
| 3,779,540 | 12/1973 | Boudreau | 269/322 X |
| 3,844,550 | 10/1974 | McGuire | 128/845 X |
| 3,897,345 | 7/1975 | Foster | 378/208 |
| 3,924,282 | 12/1975 | Bond | 5/431 |
| 3,933,154 | 1/1976 | Cabansag | 378/208 X |
| 3,938,205 | 2/1976 | Spann | 5/431 |
| 4,122,587 | 10/1978 | Weiss et al. | 378/208 X |
| 4,584,730 | 4/1986 | Rajan | 5/431 |
| 4,796,315 | 1/1989 | Crew | 5/431 |

Primary Examiner—Richard J. Apley
Assistant Examiner—Linda C. M. Dvorak
Attorney, Agent, or Firm—Michael, Best & Friedrich

[57] ABSTRACT

A portable positioning device for supporting and holding a patient in a lateral decubitus position on the table of a densitometer or the like includes a rigid back support having a vertical wall, a buttocks support having a vertical wall extending laterally at an angle relative to the vertical wall of the back support and a restraining means for holding the patient against these vertical walls, such as a flexible strap. The positioning device is placed on the densitometer table with the vertical wall of the back support parallel to the longitudinal axis of the table and the patient is positioned on the table in a lateral decubitus position and legs flexed with his or her back against the back support, buttocks against the buttocks support and knees bent in a comfortable position. The strap is wrapped around the patient's waist, pulled tight enough to hold him or her in place and then secured to the back support.

18 Claims, 2 Drawing Sheets

PATIENT POSITIONING DEVICE AND METHOD

BACKGROUND OF THE INVENTION

This invention relates to devices and methods for positioning a patient on the table of a radiation imaging machine, radiation treatment machine and the like. More particularly, the invention relates to a device and method for supporting and holding a patient in a stable lateral decubitus position on such a table.

The advantages of laterally scanning patients with x-ray devices for diagnostic purposes are well known. For instance, a paper by R. Mazess et al., "Measurement of Spine Density in the Lateral Position" presented at the First Joint Meeting of the ICCRH/ASBMR, Montreal, Canada, September 1989, discloses the use of lateral scanning for measurement of bone density in the lumbar spine region with a bone densitometer.

When patients are monitored for changes in bone density at regular intervals over a period of time, it is important for them to be in the same position and orientation for each measurement so that there is a common reference. Such a common reference is also important when different patients' measurement are compared for diagnostic purposes.

At the present time, lateral scanning usually is performed with the patient lying in the supine position. The most commonly used approach for accommodating lateral scanning is to make a C-arm carrying a radiation source and detector rotatable so that it and the radiation source and detector can be rotated 90° from the vertical. Such a capability complicates the construction of the densitometer and adds a significant cost.

It can be quite painful for patient with osteoporotic fractures to lie in the supine position on the table of a densitometer or the like for the period of time required for scanning, which typically is 5-10 minutes. On the other hand, most of such patients can lie on the table in a lateral decubitus position (i.e. on their side) with much less pain, particularly if their legs and knees are flexed into a comfortable position.

For these and other reasons, there is a need for a device and method for conveniently and repeatedly positioning patients in a comfortable, lateral decubitus position on the table of a densitometer or the like and maintaining the patient in that orientation for the period time required for scanning.

SUMMARY OF THE INVENTION

An object of the invention is to provide a positioning device and method which can be conveniently employed to repeatedly and accurately position patients in a stable, lateral decubitus position on the table of a radiation imaging machine, radiation treatment machine and the like and comfortably holding them in that orientation for some period of time.

Another object of the invention is to provide such a device which is capable of positioning and holding patients in a lateral decubitus position with his or her legs flexed at about 90° to the longitudinal axis of the body.

A further object of the invention is to provide such a device which is designed to minimize sharp discontinuities in the radiation measured by a radiation detector during scanning.

A still further object of the invention is to provide a method which is capable of repeatedly and accurately positioning and holding patients in a stable, lateral decubitus position on the table of a radiation imaging machine, radiation treatment machine and the like.

Other objects, aspects and advantages of the invention will become apparent to those skilled in the art upon reviewing the following detailed description, the drawings and the appended claims.

The invention provides a portable positioning device for supporting and holding a patient in a stable, lateral decubitus position on the table of a radiation imaging machine, radiation treatment machine or the like. The device has a rigid back support adapted to rest in a stable position on the table and including a generally vertical wall, laterally spaced from and extending generally parallel to the longitudinal axis of the table, for supporting the back of a patient lying on the table in a lateral decubitus position and restraining means cooperating with the back support for removably holding the patient's back against the vertical wall of the back support.

In one embodiment, the device also has a rigid buttocks support including a generally vertical wall, connected to and extending laterally at an angle relative to the vertical wall of the back support, preferably at a 90° angle, for supporting the buttocks of a patient lying on the table with his or her legs flexed.

The device preferably is a one-piece unit and at least the back support has radiation attenuation characteristics generally equivalent to that of soft human body tissue.

The invention also provides a method for supporting and holding a patient in a stable, lateral decubitus position on the table of a radiation imaging device, radiation treatment device or the like. The method includes the steps of placing on the table a patient positioning means including a rigid back support having a generally vertical surface which extends generally parallel to longitudinal of the axis and further including restraining means for holding the patient in a stable position with his or her back against the vertical surface, positioning the patient on the table in a lateral decubitus position with his or her lumbar spine region against the vertical surface of the back support, and moving the restraining means to a holding position.

DETAILED DESCRIPTION

The patient positioning device and method of the invention can be adapted for a wide variety of applications where it is important for a patient to be positioned and comfortably held in a stable, lateral decubitus position for some time. For example, it can be used to hold patients in a lateral decubitus position for radiographic fluoroscopy and radiation therapy. It is particularly adaptable for use in connection with lateral scanning the lumbar spine with a bone densitometer to determine bone density and will be described in connection with that application.

Figure 1:
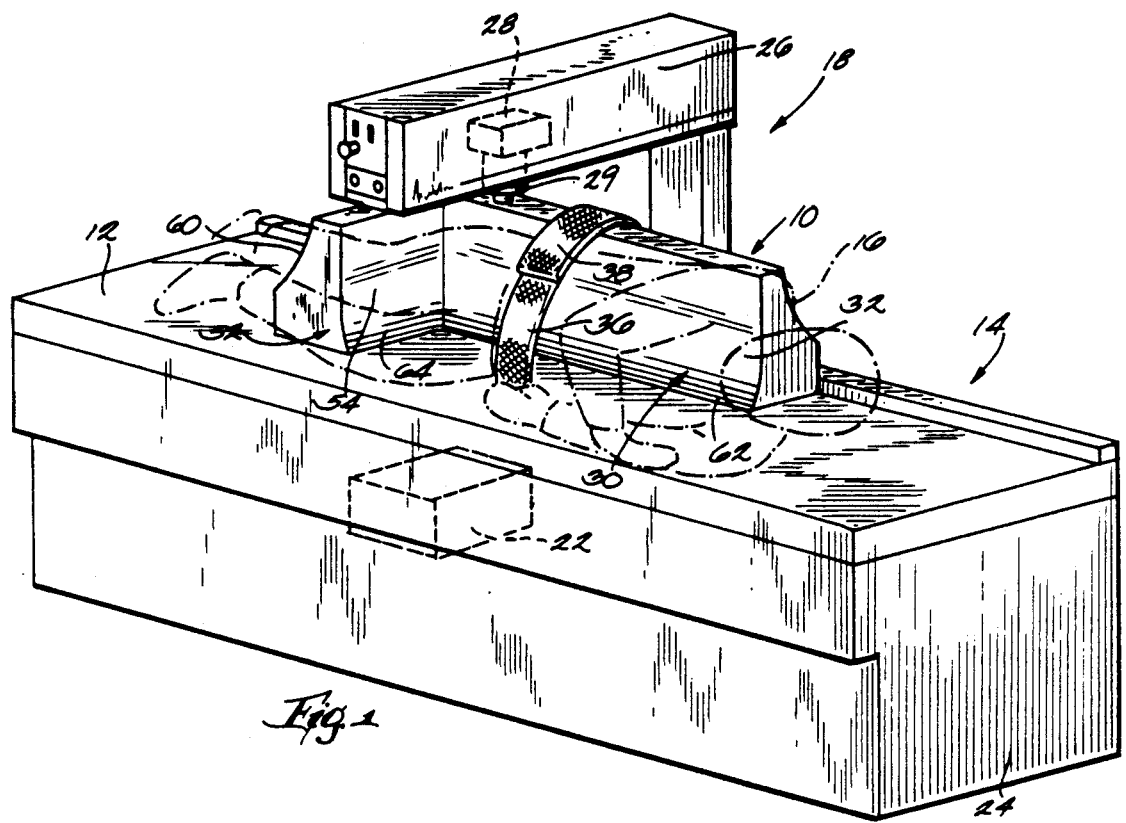
FIG. 1 is a perspective view of a positioning device embodying the invention, shown in use to support and hold a patient in a lateral decubitus position on the table of a densitometer.

FIG. 1 illustrates a patient positioning device 10 embodying the invention, shown in position on the table 12 of a conventional densitometer 14 and holding a patient 16 in a lateral decubitus position for lateral scanning of the lumbar spine.

The densitometer 14 has a C-arm 18 including a lower leg (not shown) carrying a suitable radiation source 22 inside a cabinet 24 beneath the table and an overhead leg 26 housing a conventional radiation detector 28, such as a scintillation counter. Thus, the radiation source 22 and the detector 28 are mounted in fixed relationship.

A collimated x-ray beam emitted by the radiation source 22 passes laterally through the patient 16 and impinges on the detector 28 via a window 29 which is aligned with the x-ray beam. The C-arm 18 is carried on a conventional X-Y arrangement (not shown) which permits the radiation source 22 and the detector 28 to be moved in the X and Y directions (i.e., laterally and longitudinally relative to the table 12).

To take measurements for determining bone density, the C-arm 18 is moved in the X and Y directions so that the x-ray beam laterally scans through the patient's body in a predetermined pattern (i.e., back and forth across the lumbar spine and through flesh on opposite sides of the lumbar spine and at different longitudinal increments along the length of the lumbar spine). Such scanning usually takes 5 to 10 minutes.

During this scanning operation, the detector 28 measures the attenuation characteristics of bone, flesh and other materials disposed in the path of the x-ray beam (i.e. measures the amount of x-ray transmitted through the patient and surrounding materials) and produces electrical signals representative thereof. These signals are digitized and stored in a computer (not shown) in a conventional manner. These data can be used to calculate bone density at each point in the scan pattern in any of several well known methods. Both the raw data and the calculated bone densities can be graphically displayed as an image resembling a radiograph or x-ray image by well known techniques and equipment.

Figure 2:
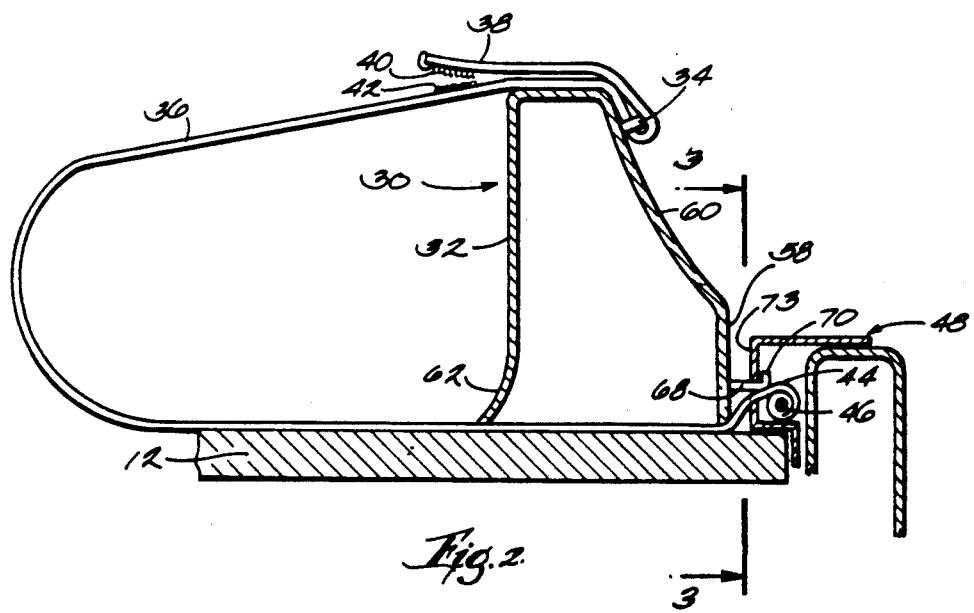
FIG. 2 is an enlarged cross sectional view of the positioning device, shown without a patient.
Figure 6:
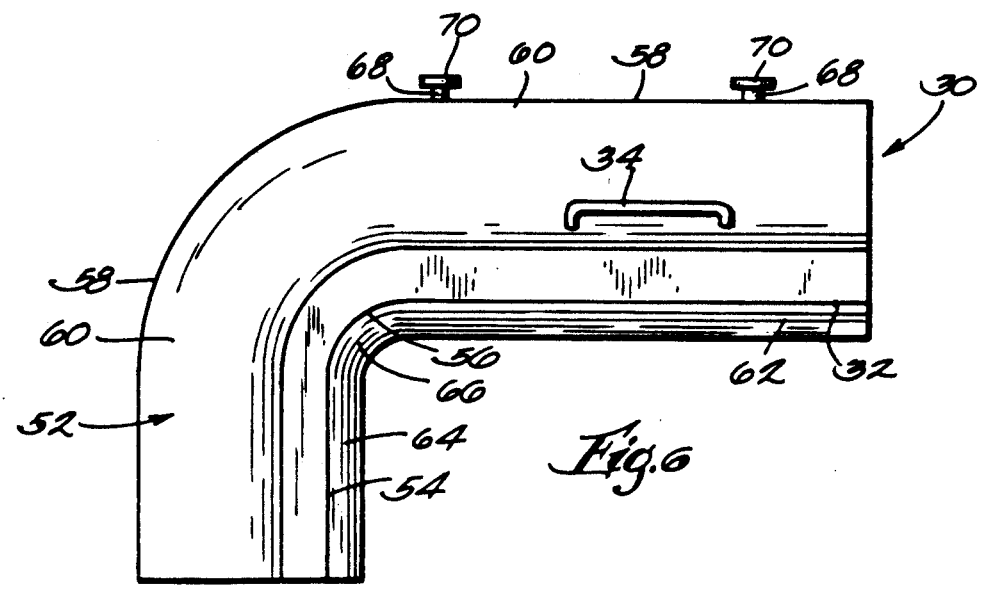
FIG. 6 is a top plan view of the positioning device in an unlocked position.

The positioning device 10 is portable and arranged so that a patient can be repeatedly and accurately positioned on the table 12 in a stable, lateral decubitus position and comfortably held in that orientation throughout scanning. As best illustrated in FIGS. 2 and 6, the positioning device 10 includes a rigid back support portion 30 adapted to rest on top and adjacent one edge of the densitometer table 12. The back support portion 30 has a generally vertical wall 32 which is laterally spaced from and extends generally parallel to the longitudinal axis of the table 12. The vertical wall 32 is of sufficient length and height to support a patient's back, particularly in the region of the lumbar spine, while lying on the table in a lateral decubitus position.

The positioning device 10 also includes restraining means for comfortably holding the patient's back against the vertical wall 32 of the back support portion 30 throughout the scanning period. While various arrangements can be used for this purpose, in the specific embodiment illustrated, the positioning device 10 includes a carrying handle 34 on the back support portion 30 and the restraining means includes a wide fabric strap 36 which extends beneath the back support portion 30 and is wrapped around the patient's waist. The free end 38 of the strap 36 is threaded through and wrapped around the handle 34, pulled tight enough to comfortably hold the patient's back against the vertical wall 32 of the back support portion 30 and then releasably secured in that position. In the specific embodiment illustrated, the strap 36 is secured by enmeshing strips 40 and 42 of Velcro fastening material or another suitable fastener on the adjoining surfaces of the strap 36.

In the specific embodiment illustrated, the opposite end 44 of the strap 36 is wound onto a spring-loaded roller 46 located beneath a bracket 48 mounted on the densitometer 14 adjacent one side of the table 12. The free end 38 of the strap 36 is threaded through an elongated horizontal slot 50 in the bracket 48 before it is wrapped around a patient's waist and secured to the back support portion 30 as described above. After use, the strap 36 is retracted onto the roller 46. If desired, the positioning device can be made self-containing by mounting the end 44 of the strap 36 directly on the back support portion 30.

The positioning device 10 preferably includes a rigid buttocks support portion 52 having a generally vertical wall 44 which is connected to and extends laterally at an angle relative to the vertical wall 32 of the back support portion 30. The vertical wall 54 of the buttocks support portion is of sufficient length and height to support a patient's buttocks when lying in a lateral decubitus position which his or her back against the back support portion 30 and legs flexed relative to the trunk. The vertical wall 54 of the buttocks support portion 52 preferably extends generally perpendicularly to the vertical wall 32 of the back support portion 30 so that the patient's legs are flexed at about 90° to the longitudinal axis of the body and the knees are bent. Such a position not only is optimum for lateral radiographically scanning the lumbar spine, it also is the most comfortable for many patients.

The positioning device 10 preferably is made from a light weight rigid material and at least the back support portion 30 is made from a material having attenuation characteristics generally equivalent to that of soft body tissue. This minimizes sharp discontinuities in the radiation measured by the detector 28 when the x-ray beam is moved beyond the posterior edge of the body during scanning. Such discontinuities can produce a visually displeasing image and cause the detector to become unstable, particularly when a higher radiation flux is being employed. Additional attenuating material can be added to the back support portion 30 in the area adjacent the lumbar spine region to further minimize such discontinuities when a high flux radiation is needed to penetrate through the lateral projection of the trunk area.

The positioning device 10 preferably is constructed as a one-piece unit and the vertical walls 32 and 54 of the back support portion 30 and the buttocks support portion 52 are the same height and are connected together by a vertical wall 56 of the same height. The wall 56 has a curvature approximating that of a patient's buttocks when or her legs are flexed at about 90° relative to the trunk.

In the specific embodiment illustrated, the positioning device 10 has a hollow construction to minimize weight and includes a continuous, outer vertical wall 58 spaced from the vertical walls 52, 54 and 56 to provide support and stability and a continuous, concave, interconnecting web section or wall 60 which acts as a stiffening rib. The positioning device 10 can be molded from a suitable rigid thermoplastic or thermosetting material having radiation attenuation characteristics generally equivalent to soft body tissue. A particularly suitable material is a glass-reinforced polyester. The positioning device 10 can have a solid construction, as long as at least the back support portion has attenuation characteristics generally equivalent to that of soft body tissue if the device is to be used with x-ray imaging machines.

When a patient is lying in a lateral decubitus position, there normally is an air gap between the posterior edge of the body and the table 12. That air gap, which substantially non-attenuating, can cause detector discontinuities. As best illustrated in FIGS. 2 and 6, the bottom portion 62 of the vertical wall 32 of the back support portion 30, and preferably the bottom portions 64 and 66 of the vertical walls 54 and 56, is curved inwardly toward the patient. This minimizes the open space between the patient's body and the positioning device 10, thereby minimizing detector discontinuities.

Figure 3:
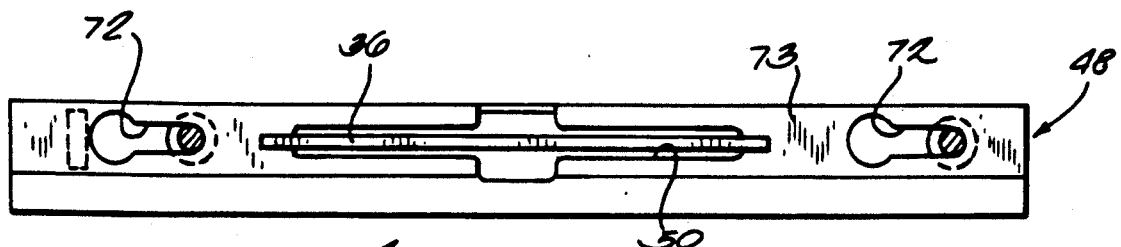
FIG. 3 is a view taken generally along line in FIG. 2 showing a bracket for locking the positioning device at a predetermined location on the densitometer table.
Figure 4:
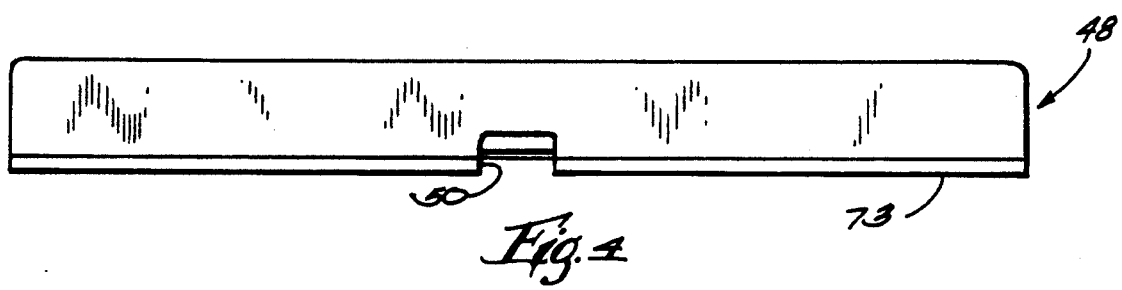
FIG. 4 is a top plan view of the bracket illustrated in FIG. 3.
Figure 5:
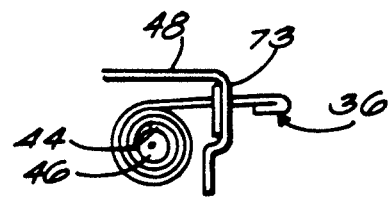
FIG. 5 is an end view of the bracket.

Means can be provided for removably locking the positioning device 10 at a predetermined location on the densitometer table 12. While various suitable arrangements can be used for this purpose, in the specific embodiment illustrated, the back support portion 30 includes a pair of longitudinally spaced lugs 68 mounted on and projecting from the outer wall 58 of the back support portion 30. The lugs 68 have enlarged heads 70 and slidably fit into horizontal, keyhole-shaped slots 72 in the front 73 of the bracket 48. The positioning device 10 is installed by registering the lug heads 70 with the enlarged portions of the slots 72 and then moving the device longitudinally until the lugs 68 "bottom out" in the slots 72 as shown in FIG. 3.

When making a scan, the free end 38 of the strap 36 is first pulled outwardly from the slot 50 and laid down across the table 12. The positioning device 10 is positioned over the strap 36 and locked into place as described above. The patient 16 is positioned on the table 12 in a lateral decubitus position, with his or her legs flexed relative to the trunk and knees bent in a comfortable position, and then moved against the back support portion 30 and the buttocks support portion 52 of the positioning device 10. A pillow or the like can be placed under the patient's head and non-attenuating cushions can be placed under the knees and the waist for comfort. The strap 36 is wrapped around the patient's waist, threaded through the handle 34 and pulled tightly against the patient and then secured as described above. The patient is held in this stable position throughout the scanning period.

From the above description, it can be seen that the positioning device and method of the invention provide several advantages. They can be conveniently employed to repeatedly and accurately position patients in the same sideway or decubitus orientation for making lateral scans or the like. The positioning device provides a rigid vertical support for the patient's back and buttocks. This enables the patient to be strapped into a stable, lateral decubitus position which is optimum for taking lateral radiographic measurements to determine bone density of the lumbar spine. The patient is held in this comfortable, stable position throughout the time period required for scanning, thereby minimizing undesirable patient movement. A patient being monitored for changes in bone density over several months or years will be in substantially the same orientation during each scanning session. Also, a patient being diagnosed for possible osteoporosis or the like will be in substantially the same orientation as prior patients. Thus, the test data in both cases has a common reference. Both AP and lateral scanning can be conveniently made on a single densitometer without the need for a rotatable C-arm carrying the radiation source and detector. Lateral scanning can be performed without causing sharp discontinuities in the radiation measured by the detector when the scanning pattern extends beyond the posterior edge of the body.

From the forgoing description, one skilled in the art can easily ascertain the essential characteristics of the invention and, without departing from the spirit and scope thereof, made various changes and modifications to adapt it to various usages.

What is claimed is:

1. A portable positioning device for supporting and holding a patient in a lateral decubitus position on the elongated table of medical diagnostic or treatment equipment, said device comprising a rigid back support portion adapted to rest in a stable position on the table for supporting and substantially immobilizing the lumbar spinal region of a patient lying on the table in a lateral decubitus position with his or her legs flexed at an angle relative to the trunk, said back support portion including a generally vertical wall which can be laterally spaced from and to extend generally parallel to the longitudinal axis of the table when said device is positioned on the table for patient diagnosis or treatment;

a rigid buttocks support portion adapted to rest in a stable position on the table and including a generally vertically wall, connected to an extending laterally at an angle relative to the vertical wall of said back support portion, for supporting the buttocks of the patient; and restraining means cooperating with said back support portion for removably holding the patient's back against the vertical wall of said back support portion.

2. A device according to claim 1 wherein the vertical wall of said buttocks support portion extends generally perpendicularly to the vertical wall of said back support portion.

3. A device according to claim 1 wherein at least said back support portion has radiation attenuation characteristics generally equivalent to that of soft human body tissue.

4. A device according to claim 3 wherein the vertical wall of said back support portion has a bottom portion which rests on the table and is curved inwardly toward the patient so as to minimize the open space between the posterior edge of the patient's body and said back support portion when the patient's back is against the vertical wall of said back portion.

5. A device according to claim 1 wherein said device is a one-piece unit.

6. A device according to claim 5 wherein the vertical walls of said back support portion and said buttocks support portion are connected together by a generally vertical wall having a curvature approximating that of a patient's buttocks when his or her legs are in a flexed position.

7. A device according to claim 1 wherein said restraining means includes a flexible strap adapted to be wrapped around the patient's body and removably secured to said back support portion.

8. A device according to claim 1 including means for removably locking said device at a predetermined location on the table.

9. A portable, one-piece device for supporting and holding a patient in a lateral decubitus position on the elongated table of a radiation imaging machine, said device being made from a rigid material and including a back support portion adapted to rest in a stable position on the table for supporting and substantially immobilizing the lumbar spinal region of a patient lying on the table in a lateral decubitus position with his or her legs flexed at an angle to the trunk, said back support portion including a generally vertical wall which can be laterally spaced from and to extend generally parallel to the longitudinal axis of the table when said device is positioned on the table for patient imaging said back support portion having radiation attenuation characteristics generally equivalent to that of soft human body tissue;

a buttocks support portion adapted to rest in a stable position on the table and including a generally vertical wall, extending laterally at an angle relative to the vertical wall of said back support portion, for supporting the buttocks of the patient;

a connecting portion including a generally vertical wall interconnecting the vertical walls of said back support portion and said buttocks support portion and having a curvature approximating that of buttocks of the patient; and restraining means cooperating with said back support portion for removably holding the patient in place on the table with his or her lumbar spinal region against the vertical wall of said back support portion and his or her buttocks against the vertical wall of said buttocks support portion.

10. A device according to claim 9 wherein the vertical wall of said back support portion has a bottom portion which rests on the table and is curved inwardly toward the patient so as to minimize the open space between the posterior edge of the patient's body and said back support portion.

11. A device according to claim 10 wherein the vertical wall of said buttocks support portion extends generally perpendicularly to the vertical wall of said back support portion.

12. A device according to claim 11 wherein said restraining means includes a flexible strap adapted to be wrapped around the patient's body and removably secured to said back support portion.

13. A device according to claim 12 including means for removably locking said device at a predetermined location on the table.

14. A method for supporting and holding a patient in a stable, lateral decubitus position on the table of a radiation imaging device to make lateral scans of the lumbar spine with the radiation imaging device, said method comprising the steps of placing on the table a patient positioning means including rigid back support having a generally vertical surface which extends generally parallel to the longitudinal axis of the table, a rigid buttocks support means having a generally vertical surface which extends laterally at an angle relative to the vertical wall of the back support and restraining means for holding a patient in a stable position with his or her lumbar spinal region against the vertical surface of said back support means;

positioning the patient on the table in a lateral decubitus position with his or her lumbar spinal region against the vertical surface of the back support, legs flexed at an angle relative to the trunk and buttocks against the vertical surface of the buttocks support; and moving the restraining means to a holding position.

15. A method according to claim 14 wherein the vertical surface of the buttocks support means extends generally perpendicularly to the vertical surface of the back support means; and the patient is positioned on the table with his or her legs flexed at 90° relative to the longitudinal axis the body.

16. A device according to claim 1 wherein the medical diagnostic or treatment equipment is a bone densitometer.

17. A device according to claim 9 wherein the radiation imaging machine is a bone densitometer.

18. A method according to claim 14 wherein the radiation imaging device is a bone densitometer.

* * * * *

UNITED STATES PATENT AND TRADEMARK OFFICE
CERTIFICATE OF CORRECTION

PATENT NO. : 5,040,546

DATED : August 20, 1991

INVENTOR(S) : James G. Deluhery

It is certified that error appears in the above-identified patent and that said Letters Patent is hereby corrected as shown below:

Column 6, line 36, the word "an" should read ---and---.

Signed and Sealed this

Fourth Day of May, 1993

Attest:

MICHAEL K. KIRK

*Attesting Officer*     Acting Commissioner of Patents and Trademarks